United States Patent
Stanchev et al.

(10) Patent No.: US 12,109,435 B2
(45) Date of Patent: Oct. 8, 2024

(54) PATIENT MARKING AND POSITIONING IN A RADIATION THERAPY SYSTEM

(71) Applicant: Varian Medical Systems, Inc., Palo Alto, CA (US)

(72) Inventors: Sevelin Stanchev, Las Vegas, NV (US); Stephen Thompson, Pacific Grove, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 709 days.

(21) Appl. No.: 17/332,938

(22) Filed: May 27, 2021

(65) Prior Publication Data

US 2022/0379140 A1 Dec. 1, 2022

(51) Int. Cl.
*A61N 5/10* (2006.01)
*A61B 6/00* (2006.01)
(Continued)

(52) U.S. Cl.
CPC .......... *A61N 5/1069* (2013.01); *A61B 6/102* (2013.01); *A61B 6/465* (2013.01); *A61B 6/469* (2013.01);
(Continued)

(58) Field of Classification Search
None
See application file for complete search history.

(56) References Cited

U.S. PATENT DOCUMENTS

| 5,117,829 A | * | 6/1992 | Miller | A61N 5/1049 378/65 |
| 7,672,429 B2 | * | 3/2010 | Urano | A61N 5/1049 378/65 |

(Continued)

FOREIGN PATENT DOCUMENTS

| EP | 1832312 A1 | 9/2007 |
| EP | 1972360 A2 | 9/2008 |
| WO | 90/11721 A1 | 10/1990 |

OTHER PUBLICATIONS

International Search Report and Written Opinion of the International Searching Authority, International application No. PCT/US2022/025857, Jul. 20, 2022.

*Primary Examiner* — Thomas R Artman
(74) *Attorney, Agent, or Firm* — SU IP CONSULTING

(57) ABSTRACT

An example method for a radiation therapy system that includes a movable couch to perform radiation therapy has been disclosed. One method includes based on the X-ray images of an anatomical region of the patient that includes a target volume, reconstructing a digital volume of the anatomical region and based on a user input indicating a location of a patient origin in the digital volume, determining one or more shift values for repositioning the patient origin at an isocenter of the radiation therapy system with respect to a coordinate system. The method also includes obtaining a treatment plan that is based on the location of the patient origin and is associated with the target volume, based on the treatment plan, repositioning the movable couch so that the patient origin is disposed at the isocenter, and while (Continued)

the patient origin is disposed at the isocenter, directing a treatment beam to the patient origin in accordance with the treatment plan associated with the target volume.

19 Claims, 15 Drawing Sheets

(51) Int. Cl.
 *A61B 6/10* (2006.01)
 *A61B 6/46* (2024.01)
(52) U.S. Cl.
 CPC ............ *A61B 6/548* (2013.01); *A61N 5/1049* (2013.01); *A61N 5/1081* (2013.01); *A61N 2005/1062* (2013.01); *A61N 2005/1074* (2013.01)

(56) References Cited

U.S. PATENT DOCUMENTS

| | | | | |
|---|---|---|---|---|
| 8,300,907 B2* | 10/2012 | Nagamine | ............ | A61N 5/1048 128/923 |
| 8,315,356 B2* | 11/2012 | Core | .................... | A61N 5/1049 378/65 |
| 10,888,714 B2* | 1/2021 | Dempsey | ............. | A61N 5/1037 |
| 11,135,452 B2* | 10/2021 | Zhou | .................... | A61B 6/4085 |
| 11,612,767 B2* | 3/2023 | Zhou | ..................... | A61B 6/566 378/65 |
| 11,628,314 B2* | 4/2023 | Dempsey | ................ | A61N 5/107 600/1 |
| 2007/0211856 A1* | 9/2007 | Urano | ................. | A61N 5/1049 378/65 |
| 2008/0232664 A1* | 9/2008 | Nagamine | ........... | A61N 5/1048 382/131 |
| 2012/0069968 A1* | 3/2012 | Core | ................... | A61N 5/1049 378/206 |
| 2016/0228728 A1* | 8/2016 | Dempsey | ............ | A61N 5/1071 |
| 2019/0175943 A1* | 6/2019 | Dempsey | ............ | A61N 5/1064 |
| 2019/0336795 A1 | 11/2019 | Zhou et al. | | |
| 2020/0390406 A1* | 12/2020 | Xu | ........................ | A61B 6/547 |
| 2021/0146160 A1* | 5/2021 | Dempsey | ............ | A61N 5/1071 |
| 2022/0016443 A1* | 1/2022 | Zhou | ................... | A61N 5/1038 |
| 2022/0379140 A1* | 12/2022 | Stanchev | ............ | A61N 5/1049 |

* cited by examiner

PATIENT MARKING AND POSITIONING IN A RADIATION THERAPY SYSTEM

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. For example, a treatment planning scan is often performed via computed tomography (CT) to generate the three-dimensional image. From such imaging, the size and mass of the target tissue can be estimated, a planning target volume determined, and an appropriate treatment plan generated.

So that the prescribed dose is correctly supplied to the planning target volume during radiation therapy, a patient must be correctly positioned relative to the linear accelerator that provides the radiation therapy. Typically, the patient must be precisely positioned so that the planning target volume is located at the isocenter about which the linear accelerator rotates. To that end, the location of the planning target volume is pinpointed when the treatment planning images are generated, and external patient markings are made that indicate the location of the planning target volume at the time of treatment. For example, based on the location of the planning treatment volume determined via treatment planning images, a laser-based system can indicate precise locations on the patient for external markings that have a specified relationship to the planning treatment volume. Such external patient markings enable the correct positioning of the patient, and therefore the planning target volume, with respect to a linear accelerator isocenter at the time of treatment.

However, even with the use of external patient markings, accurately positioning a patient at time of treatment can be prone to certain errors that necessitate re-planning of the patient and/or repeating treatment planning imaging. According to analysis of the Radiation Oncology Incident Learning System (RO-ILS), two of the three major error pathways leading to an incorrect radiation treatment are "wrong shift instructions" and "wrong shift performed at treatment."

"Wrong shift instruction" errors can occur when the location of a planning target volume is incorrectly converted from the coordinate system of a treatment planning imager to the coordinate system of an associated laser-marking system, resulting in erroneous locations for external patient markings. Frequently, incorrect conversions occur due to human error in the various steps of the patient-marking process, such as calculating the shift needed to position the planning treatment volume in a particular position for laser marking, manually entering location information from one coordinate system into another system, positioning one or more lasers of the laser-marking system, etc. Such errors are generally detected during treatment planning, but at that point the patient has been marked with incorrectly located external markings. Consequently, to compensate for the incorrectly located external markings, an additional shift must be applied to patient position relative to the treatment system alignment lasers, which is a procedure that can be an additional source of error.

"Wrong shift performed at treatment" errors can occur when a tumor or other planning target volume is located with a large offset from the center of the treatment planning images. In some instances, a physical shift of the radiation treatment system couch that is needed to compensate for such an offset exceeds the range of motion of the couch and/or results in a collision with a portion of the radiation treatment system. For example, the planning target volume may be determined via a treatment planning image to be laterally offset many centimeters from a center location in the field of view of the treatment planning image. To enable locating such a planning target volume at the isocenter of a radiation therapy system during treatment, external patient markings are placed on the patient that, when aligned with a light field of the radiation therapy system, position the planning target volume at the isocenter. However, because marking lasers associated with the imaging system are employed to indicate the locations for the external patient markings, such locations may indicate a position for the patient that cannot be implemented by the movable couch of the radiation therapy system. That is, when the patient is disposed on the movable couch of the radiation therapy system, the external patient markings may indicate a lateral translation that exceeds the range of motion of the movable couch, and therefore cannot be performed by the radiation therapy system.

Further, because the bore of the imager used to generate the treatment planning images can have a significantly different geometry than that of the radiation therapy system that provides the radiation treatment, the external patient markings may indicate a couch position of the radiation therapy system that results in a collision between a patient and the bore or other component of the radiation therapy system. Thus, it is generally common practice at many institutions to perform a "dry run" of the patient's treatment, during which the patient is positioned and loaded prior to a treatment session to ensure the current treatment plan is collision-free. Such dry runs ensure a treatment plan is collision-free and deliverable for the patient, but requires additional utilization time of the radiation therapy system, which is typically very limited.

In light of the above, there is a need in the art for techniques to accurately mark a patient when treatment planning images are acquired and accurately position a patient at time of treatment.

SUMMARY

In accordance with at least some embodiments, a radiation therapy system is configured to image patient anatomy surrounding a planning target volume, reconstruct a digital volume of the patient anatomy, and facilitate the selection of a DICOM origin. In the embodiments, the radiation therapy system is further configured to facilitate positioning a patient so that the DICOM origin is disposed at the isocenter of the radiation therapy system and to perform radiation therapy as set forth in a treatment plan based on the DICOM origin.

In accordance with at least some embodiments, a method for a radiation therapy system that includes a movable couch to perform radiation therapy in a coordinate system includes: based on the X-ray images of an anatomical region of the patient that includes a target volume, reconstructing a digital volume of the anatomical region; based on a user input indicating a location of a patient origin in the digital volume, determining one or more shift values for repositioning the patient origin at an isocenter of the radiation therapy system with respect to the coordinate system; obtaining a treatment plan that is based on the location of the patient origin and is associated with the target volume; based on the treatment plan, repositioning the movable couch so that the patient origin is disposed at the isocenter; and while the patient origin is disposed at the isocenter, directing a treatment beam to the patient origin in accordance with the treatment plan associated with the target volume.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
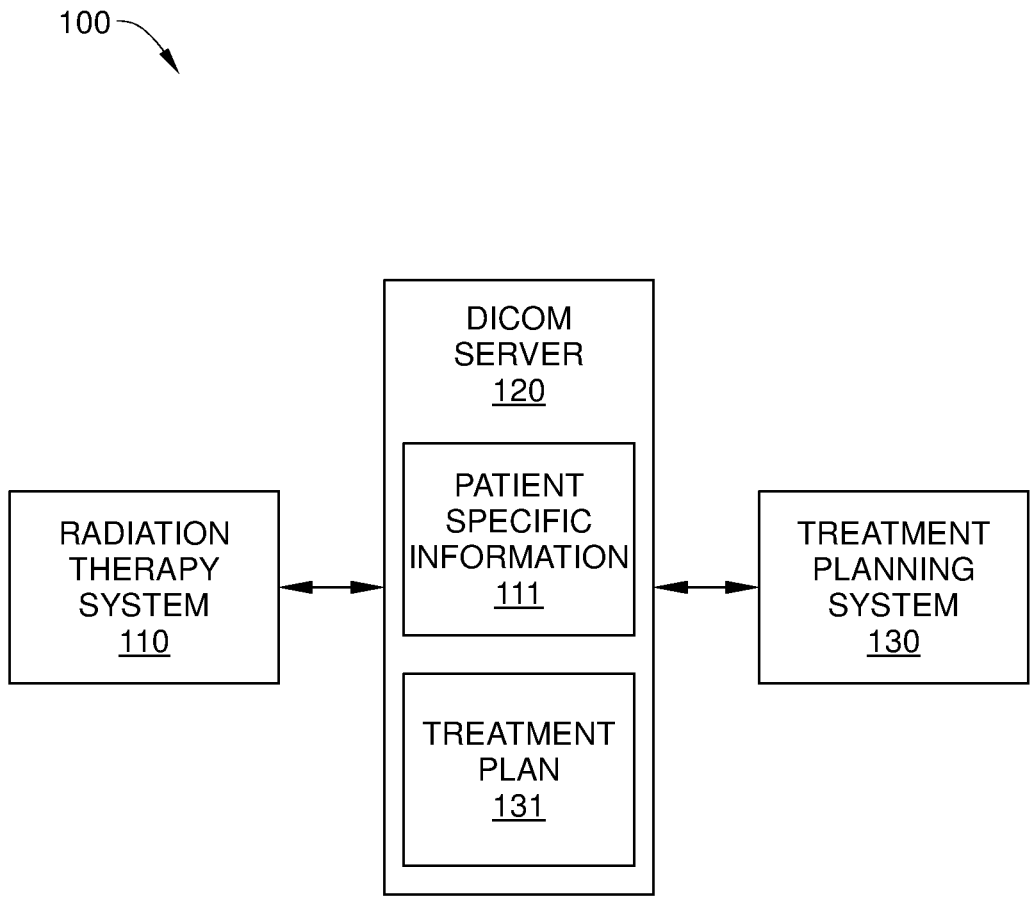
FIG. 1 is a block diagram illustrating a radiation therapy network, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a block diagram illustrating a radiation therapy network 100, according to various embodiments. Radiation therapy network 100 is configured to perform a radiation therapy process, including generating patient image, patient origin, and couch shift information prior to radiation therapy, performing planning treatment based on the patient image and patient origin information to generate a radiation treatment plan, and implementing the radiation treatment plan at time of treatment. To that end, radiation therapy network 100 includes a radiation therapy system 110, one or more Digital Imaging and Communications in Medicine (DICOM) servers 120, and a treatment planning system 130.

Radiation therapy (RT) system 110 is configured to image patient anatomy surrounding a planning target volume, such as a tumor, and reconstruct a digital volume of the patient anatomy that includes the planning target volume. In some embodiments, RT system 110 performs such imaging via a cone-beam computed tomography (CBCT) process using one or more imagers incorporated in RT system 110, such as one or more kilovolt (kV) X-ray imagers. RT system 110 is further configured to facilitate the selection of a DICOM origin, referred to herein as a "patient origin," which is generally positioned at an isocenter of RT system 110 during treatment. Specifically, RT system 110 is configured to display one or more portions of the reconstructed digital volume to enable viewing of the location of the planning target volume by a user. Examples of such portions include one or more of a sagittal (or longitudinal) slice, a transversal (or axial) slice, and/or a coronal (or frontal) slice of the digital volume. Based on such slices, prior to the treatment planning process a user can define a patient origin that should be within the planning target volume and couch shift values that position the planning target volume at the isocenter of RT system 110. The patient origin, couch coordinates that are based in part on the couch shift values, and image information for the digital volume can then be saved in DICOM server 120 as patient-specific information 111. RT system 110 is also configured to facilitate positioning a patient so that the DICOM origin is disposed at the isocenter of RT system 110 and perform radiation therapy as set forth in a treatment plan 131 stored in DICOM server 120.

DICOM server 120 is configured to save patient-specific information 111, such as patient origin and image information, and treatment plan 131 as shown. DICOM server 120 is further configured to adhere to the DICOM standard for the communication and management of medical imaging information and related data.

Treatment planning system 130 is configured to generate a treatment plan 131 for a particular patient, typically in response to a diagnosis for a patient that indicates the patient is to be treated via external beam radiation therapy. The diagnosis typically indicates external beam radiation therapy (instead of internal radiation therapy) based on various factors, including: the type of cancer tumor that has been detected, the size of the detected tumor, the location of the tumor in the body, proximity of the tumor to organs at risk (OARs) or other normal tissues that are sensitive to radiation, the general health and medical history of the patient, the presence of other types of cancer in the patient, the age of the patient, certain medical conditions of the patient, and the like. Treatment planning system 130 includes one or more software applications for performing and/or assisting in the performance of various processes associated with treatment planning, such as generation of a treatment planning directive, target segmentation, organs-at-risk (OAR) segmentation, treatment plan optimization, and/or the like.

The treatment planning directive typically describes image studies for a treatment site, including target tissue structures and normal tissue structures to be defined via the imaging studies. These target and normal tissue structures are subsequently used for treatment planning. In addition, in some instances, the treatment planning directive may specify the gross tumor volume (GTV), the clinical target volume (CTV), the internal target volume (ITV), the planning target volume (PTV), OARs, and/or a planning organ at risk volume (PRV), among others. In treatment plan optimization, one or more beam geometries for implementing the planned treatment is determined and a dose distribution for each beam geometry is optimized.

Figure 2:
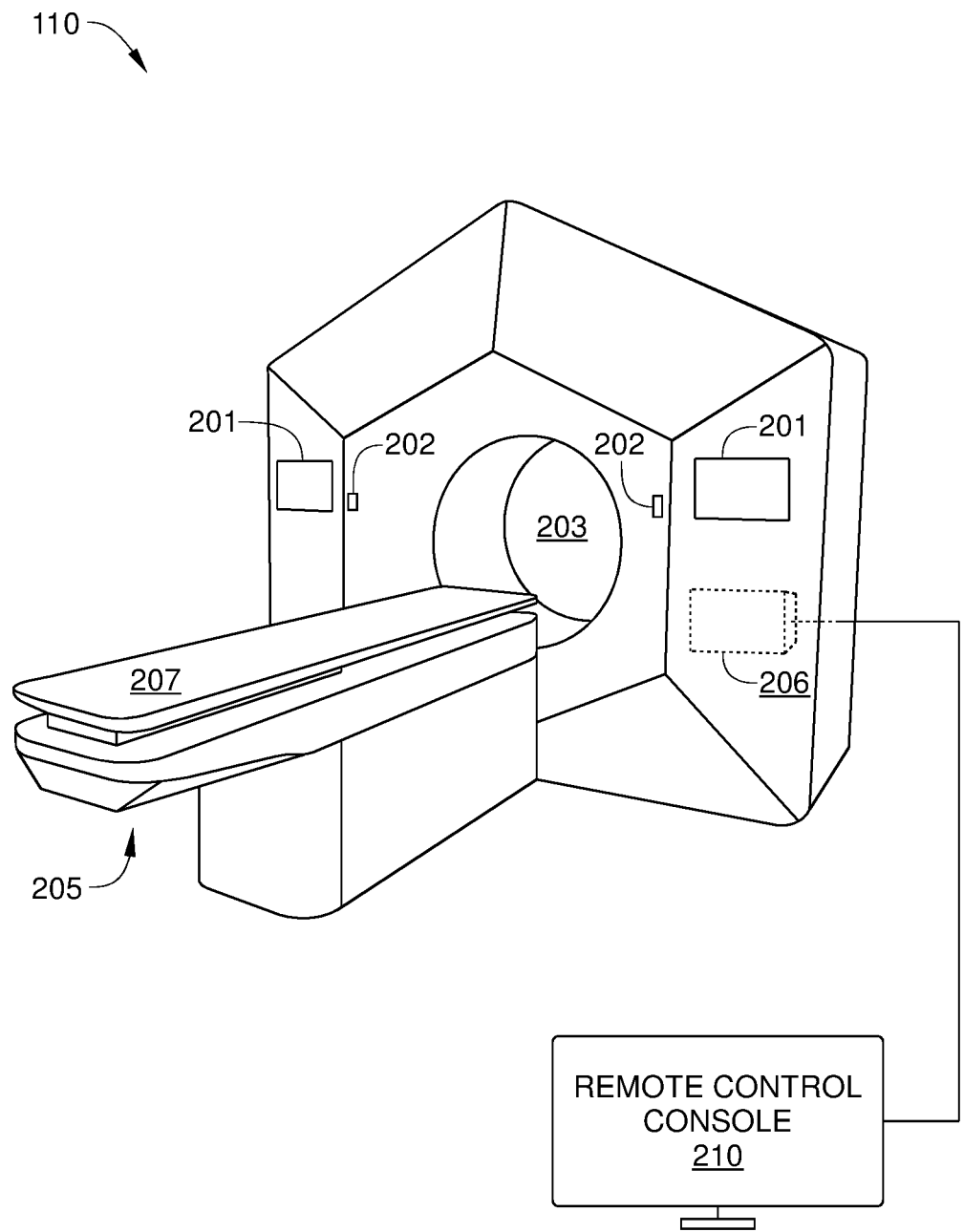
FIG. 2 is a perspective view of a radiation therapy system, according to various embodiments.

FIG. 2 is a perspective view of RT system 110, according to various embodiments. In some embodiments, radiation therapy (RT) system 110 is a radiation system configured to detect inter-fraction motion intra-fraction motion using X-ray imaging techniques. Thus, RT system 110 is configured to provide stereotactic radiosurgery and precision radiotherapy for lesions, tumors, and conditions anywhere in the body where radiation treatment is indicated. As such, RT system 110 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, RT system 110 is described herein configured with a circular gantry. In other embodiments, RT system 110 can be configured with a C-gantry capable of infinite rotation via a slip ring connection.

Generally, RT system 110 is capable of kV imaging of a target volume, to generate treatment planning image information and/or to generate images during a radiation therapy treatment fraction. Thus, in some embodiments, RT system 110 can be employed in addition to or instead of a treatment planning computed tomography imager. Further, in some embodiments, RT system is configured to image a target volume immediately prior to and/or during application of an MV treatment beam, so that an image-guided radiation therapy (IGRT) process and/or an intensity-modulated radiation therapy (IMRT) process can be performed using X-ray imaging. RT system 110 may include one or more touchscreens 201, couch motion controls 202, a bore 203, a base positioning assembly 205, a couch 207 disposed on base positioning assembly 205, and an image acquisition and treatment control computer 206, all of which are disposed within a treatment room. RT system 110 further includes a remote control console 210, which is disposed outside the treatment room and enables treatment delivery and patient monitoring from a remote location. Base positioning assembly 205 is configured to precisely position couch 207 with respect to bore 203, and motion controls 202 include input devices, such as button and/or switches, that enable a user to operate base positioning assembly 205 to automatically and precisely position couch 207 to a predetermined location with respect to bore 203. Motion controls 202 also enable a user to manually position couch 207 to a predetermined location.

In some embodiments, RT system 110 does not include a conventional light field or isocenter lasers disposed in bore 203, but instead is configured with setup lasers (not shown for clarity) that are included in RT system 110, but are disposed outside of bore 203. In some embodiments, the setup lasers are employed for initial patient setup outside of bore 203 prior to radiation treatment. In such embodiments, a patient is positioned on couch 207 in an initial position, in which external patient markings are aligned with the setup lasers. Thus, when the patient is in the initial position, the patient (and patient origin) is in a known location relative to the coordinate system that is associated with couch 207 and also with RT system 110 generally. The patient is then loaded from the initial position to a treatment position through predefined couch shifts, so that the patient origin is positioned at the isocenter of RT system 110 during treatment. Such predefined couch shifts vary depending on which particular RT system 110 is employed, and indicate the differences in location between the initial position for a particular RT system 110 (i.e., where the patient is first positioned on couch 207) and the treatment position for that particular RT system 110 (i.e., where the patient undergoes radiation therapy). It is noted that such predefined couch shifts are generally fixed for a particular RT system 110, and are distinct from the couch shift values that are determined as described below in conjunction with FIGS. 6, 7A, 7B, and 7C. In some embodiments, the setup lasers of RT system 110 are employed for indicating the appropriate locations of external patient markings immediately after treatment planning images are generated by RT system 110. In such embodiments, a patient is unloaded from an imaging position, in which a center location in the field of view of RT system 110 is located at the isocenter of RT system 110, to the initial position, where the setup lasers then indicate locations for the external patient markings. Typically, once the patient has been unloaded to the initial position from the imaging position, appropriately located external patient markings are placed on the patient.

Figure 3:
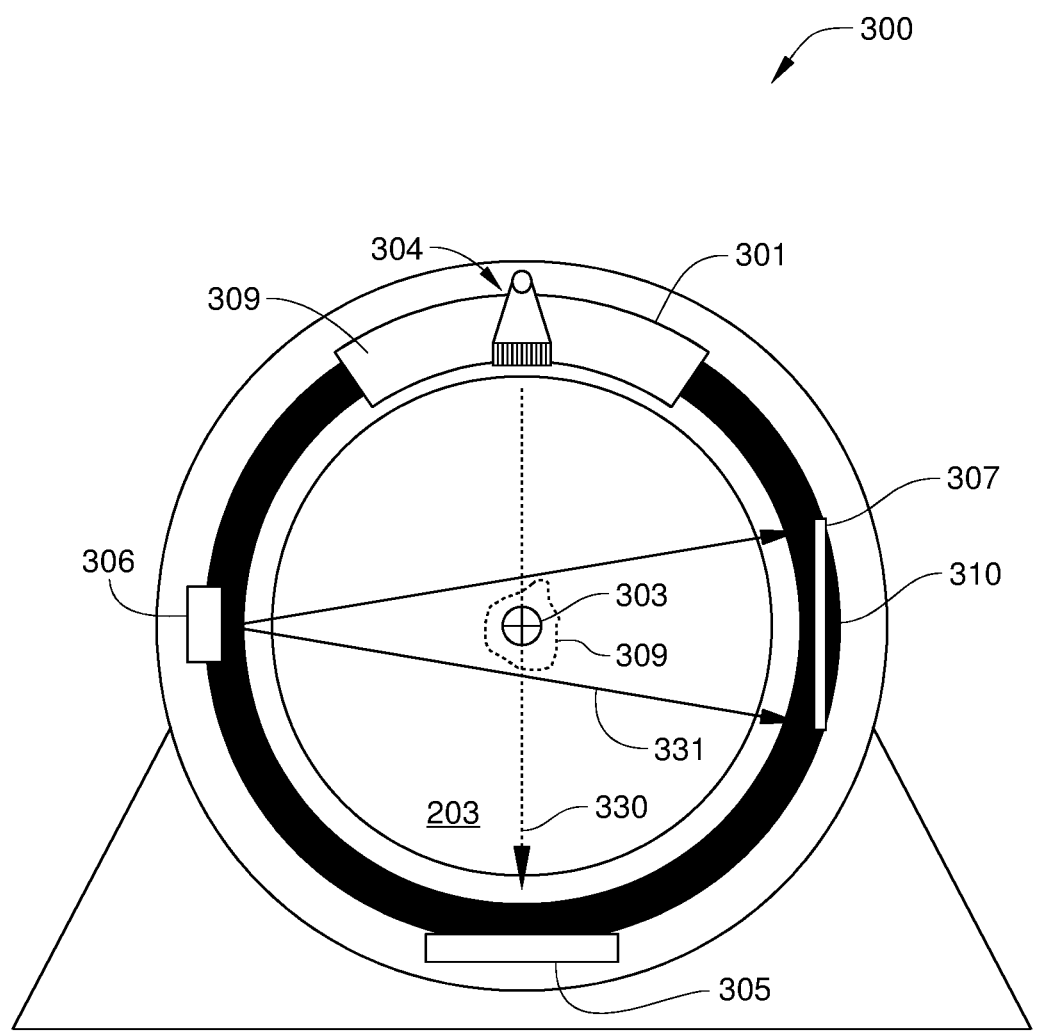
FIG. 3 schematically illustrates a drive stand and gantry of the radiation therapy system of FIG. 2, according to various embodiments.

FIG. 3 schematically illustrates a drive stand 300 and gantry 310 of RT system 110, according to various embodiments. Covers, base positioning assembly 205, couch 207, and other components of RT system 110 are omitted in FIG. 3 for clarity. Drive stand 300 is a fixed support structure for components of RT treatment system 210, including gantry 310 and a drive system 301 for rotatably moving gantry 310. Drive stand 300 rests on and/or is fixed to a support surface that is external to RT system 110, such as a floor of an RT treatment facility. Gantry 310 is rotationally coupled to drive stand 300 and is a support structure on which various components of RT system 110 are mounted, including a linear accelerator (LINAC) 304, an MV electronic portal imaging device (EPID) 305, an imaging X-ray source 306, and an X-ray imager 307. During operation of RT system 110, gantry 320 rotates about bore 203 when actuated by drive system 301.

Drive system 301 rotationally actuates gantry 310. In some embodiments, drive system 301 includes a linear motor that can be fixed to drive stand 300 and interacts with a magnetic track (not shown) mounted on gantry 310. In other embodiments, drive system 301 includes another suitable drive mechanism for precisely rotating gantry 310 about bore 301. LINAC 304 generates an MV treatment beam 330 of high energy X-rays (or in some embodiments electrons, protons, and/or other heavy charged particles, ultra-high dose rate X-rays (e.g., for FLASH radiotherapy) or microbeams for microbeam radiation therapy) and EPID 305 is configured to acquire X-ray images with treatment beam 330. Imaging X-ray source 306 is configured to direct a conical beam of X-rays, referred to herein as imaging X-rays 331, through an isocenter 303 of RT system 110 to X-ray imager 307, and isocenter 303 typically corresponds to the location of a target volume 309 to be treated. In the embodiment illustrated in FIG. 3, X-ray imager 307 is depicted as a planar device, whereas in other embodiments, X-ray imager 307 can have a curved configuration.

X-ray imager 307 receives imaging X-rays 331 and generates suitable projection images therefrom. According to certain embodiments, such projection images can then be employed to construct or update portions of imaging data for a digital volume that corresponds to a three-dimensional (3D) region that includes target volume 309. That is, a 3D image of such a 3D region is reconstructed from the projection images. In some embodiments, cone-beam computed tomography (CBCT) and/or digital tomosynthesis (DTS) can be used to process the projection images generated by X-ray imager 307. CBCT is typically employed to acquire projection images over a relatively long acquisition arc, for example over a rotation of 180° or more of gantry 310. As a result, a high-quality 3D reconstruction of the imaged volume can be generated. In some embodiments, CBCT can be employed to generate treatment planning images. Additionally or alternatively, in some embodiments, CBCT is employed at the beginning of a radiation therapy session to generate a set-up 3D reconstruction. For example, CBCT may be employed immediately prior to application of treatment beam 330 to generate a 3D reconstruction confirming that target volume 309 has not moved or changed shape. Alternatively, or additionally, in some embodiments, partial-data reconstruction is performed by RT system 110 during portions of an IGRT or IMRT process in which partial image data is employed to generate a 3D reconstruction of target volume 309. For example, as treatment beam 330 is directed to isocenter 303 while gantry 310 rotates through a treatment arc, DTS image acquisitions can be performed to generate image data for target volume 309. Because DTS image acquisition is performed over a relatively short acquisition arc, for example between about 10° and 60°, near real-time feedback for the shape and position of target volume 309 can be provided by DTS imaging during the IGRT process.

In the embodiment illustrated in FIG. 3, RT system 110 includes a single X-ray imager and a single corresponding imaging X-ray source. In other embodiments, RT system 110 can include two or more X-ray imagers, each with a corresponding imaging X-ray source. One such embodiment is illustrated in FIG. 4.

Figure 4:
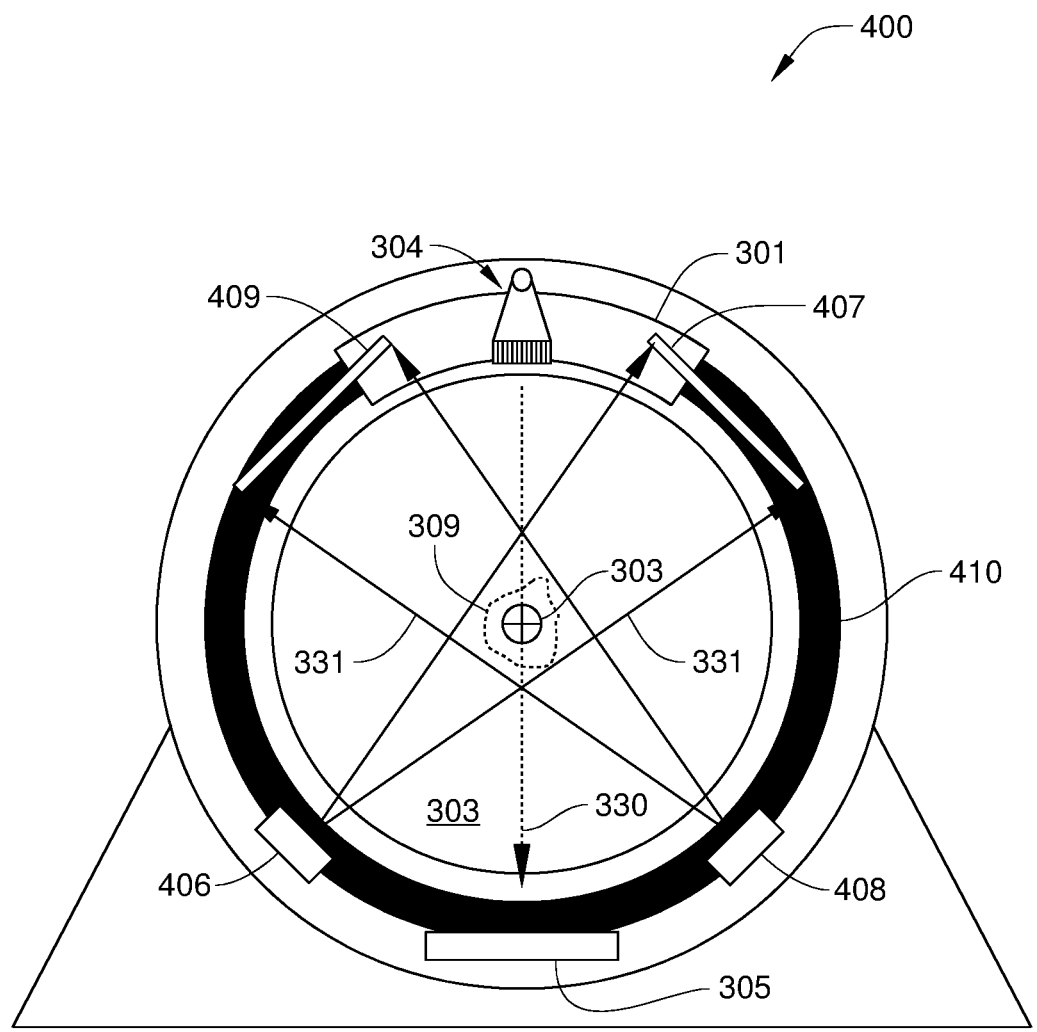
FIG. 4 schematically illustrates a drive stand and a gantry of the radiation therapy system of FIG. 2, according to various embodiments.

FIG. 4 schematically illustrates a drive stand 400 and gantry 410 of RT system 110, according to various embodiments. Drive stand 400 and gantry 410 are substantially similar in configuration to drive stand 300 and gantry 310 in FIG. 3, except that the components of RT system 110 that are mounted on gantry 410 include a first imaging X-ray source 406, a first X-ray imager 407, a second imaging X-ray source 408, and a second X-ray imager 409. In such embodiments, the inclusion of multiple X-ray imagers in RT system 110 facilitates the generation of projection images (for reconstructing the target volume) over a shorter image acquisition arc. For instance, when RT system 110 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 307 (or by first x-ray imager 407 and second X-ray imager 409) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 5.

Figure 5:
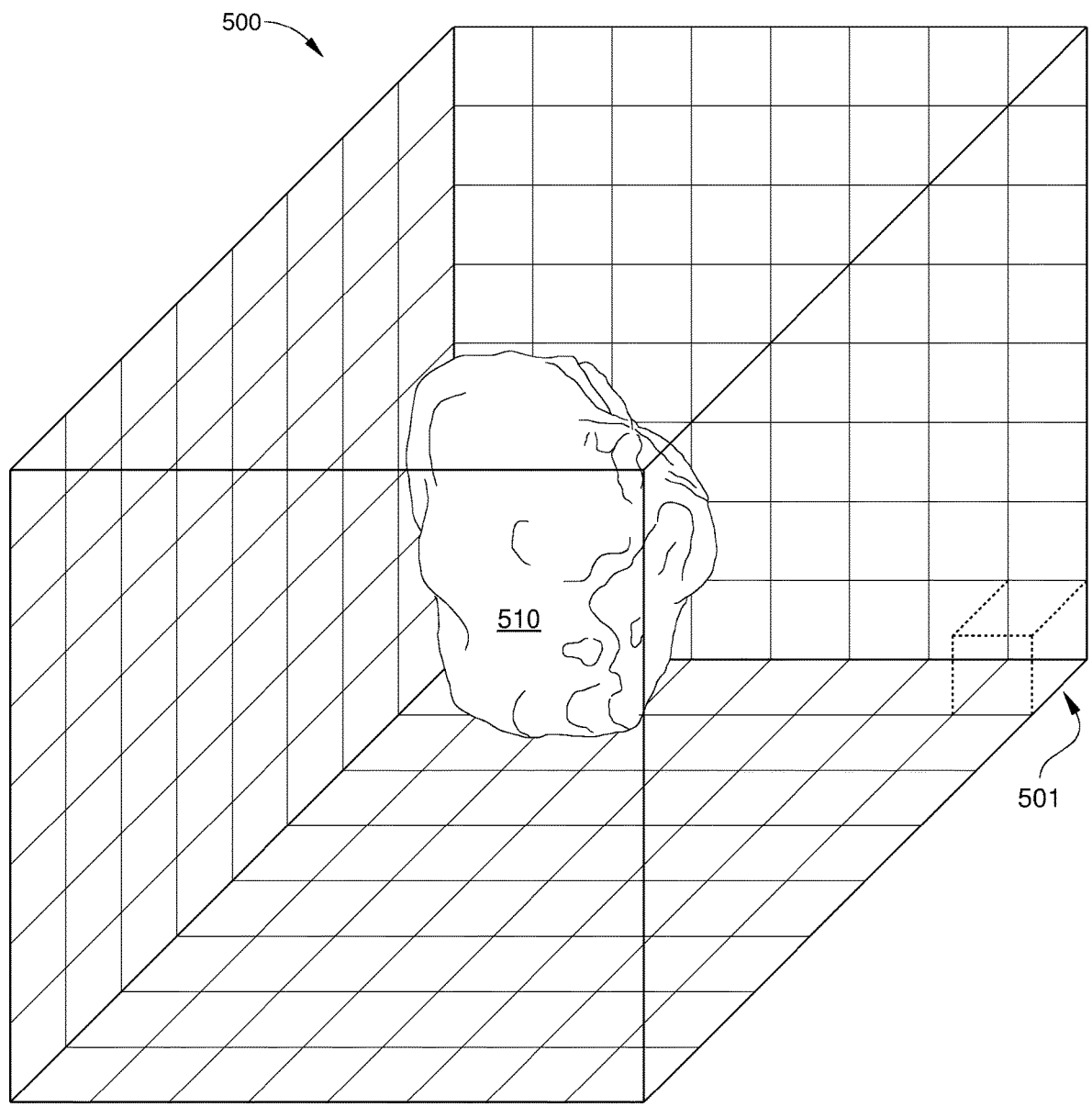
FIG. 5 schematically illustrates a digital volume that is constructed based on projection images generated by one or more X-ray images included in the radiation therapy system of FIG. 2, according to various embodiments.

FIG. 5 schematically illustrates a digital volume 500 that is constructed based on projection images generated by one or more X-ray imagers included in RT system 110, according to various embodiments. For example, in some embodiments, the projection images can be generated by a single X-ray imager, such as X-ray imager 307, and in other embodiments the projection images can be generated by multiple X-ray imagers, such as first x-ray imager 407 and second X-ray imager 409.

Digital volume 500 includes a plurality of voxels 501 (dashed lines) of anatomical image data, where each voxel 501 corresponds to a different location within digital volume 500. For clarity, only a single voxel 501 is shown in FIG. 5. Digital volume 500 corresponds to a 3D region that includes target volume 510. In FIG. 5, digital volume 500 is depicted as an 8×8×8 voxel cube, but in practice, digital volume 500 generally includes many more voxels, for example orders of magnitude more than are shown in FIG. 5.

For purposes of discussion, target volume 510 can refer to the GTV, CTV, or the PTV for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 500.

According to various embodiments described below, image information associated with each voxel 501 of digital volume 500 is constructed via projection images generated by the single or multiple X-ray imagers via a CBCT process. For example, such a CBCT process can be employed immediately prior to delivering treatment beam 330 to target volume 510, so that the location and shape of target volume 510 can be confirmed before treatment begins. In addition, according to various embodiments, image information associated with some or all of voxels 501 of digital volume 500 is updated via projection images generated by the single or multiple X-ray imagers via a DTS process. For example, such a DTS process can be employed after a portion of a planned treatment has begun and before the planned treatment has completed. In this way, the location and shape of target volume 510 can be confirmed while the treatment is underway. Thus, if a sufficient portion of the target volume 510 is detected to be extending outside a threshold region, the treatment can either be aborted or modified. In such an instance, modification of the treatment can be accomplished by adjusting patient position and/or the treatment beam.

Determination of Couch Shift Values

According to various embodiments, a radiation therapy system is configured to image patient anatomy surrounding a planning target volume, reconstruct a digital volume of the patient anatomy that includes the planning target volume, and enable the user definition of a patient origin. The radiation therapy system is further configured to determine couch shift values associated with a selected patient origin. The image information (e.g., the reconstructed digital volume), the patient origin information, and the couch coordinates based in part on the couch shift values are then stored in a DICOM server for subsequent treatment planning. One such embodiment is described below in conjunction with FIG. 6.

Figure 6:
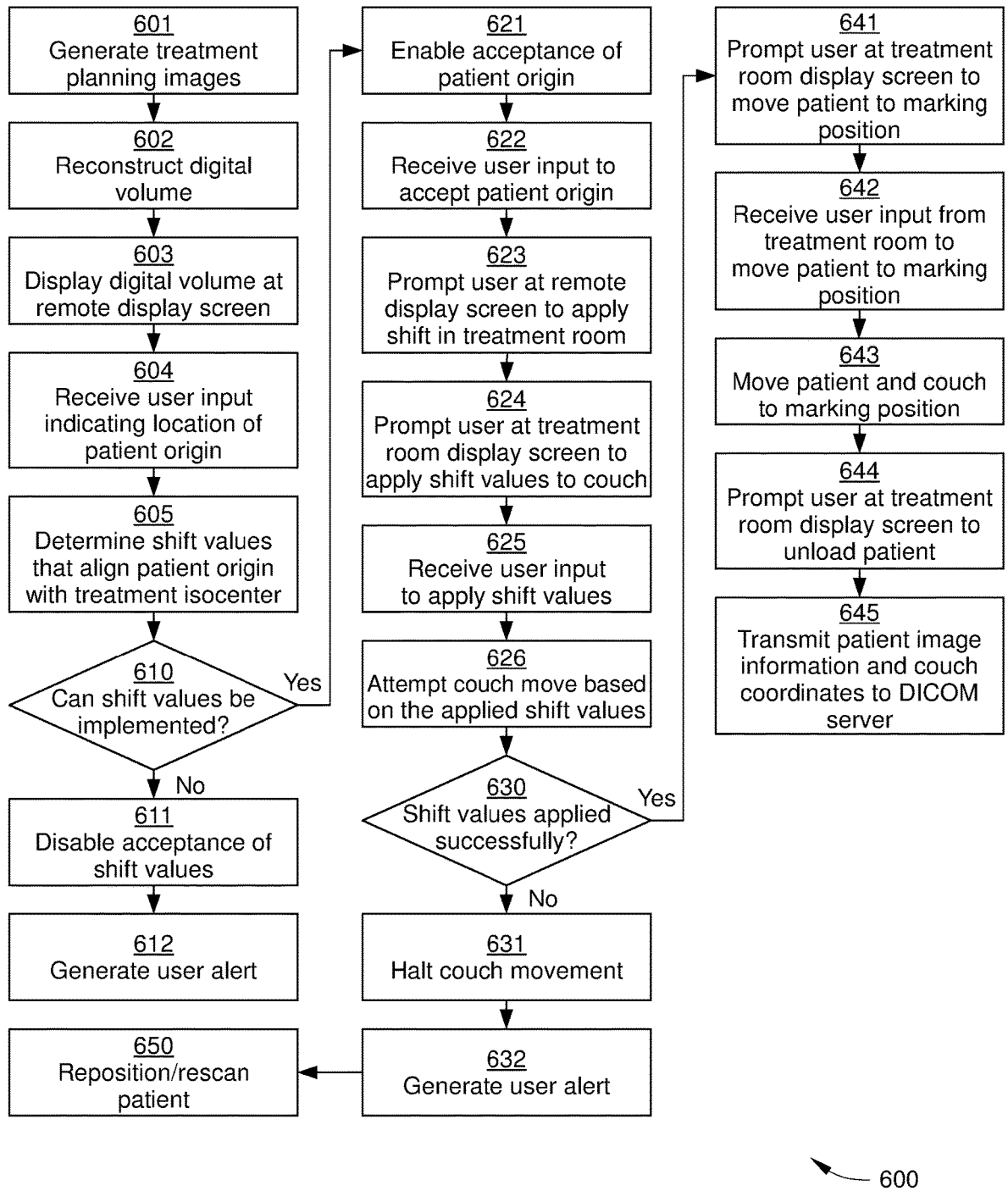
FIG. 6 sets forth a flowchart of a method for a radiation therapy system, according to one or more embodiments.
Figure 7A:
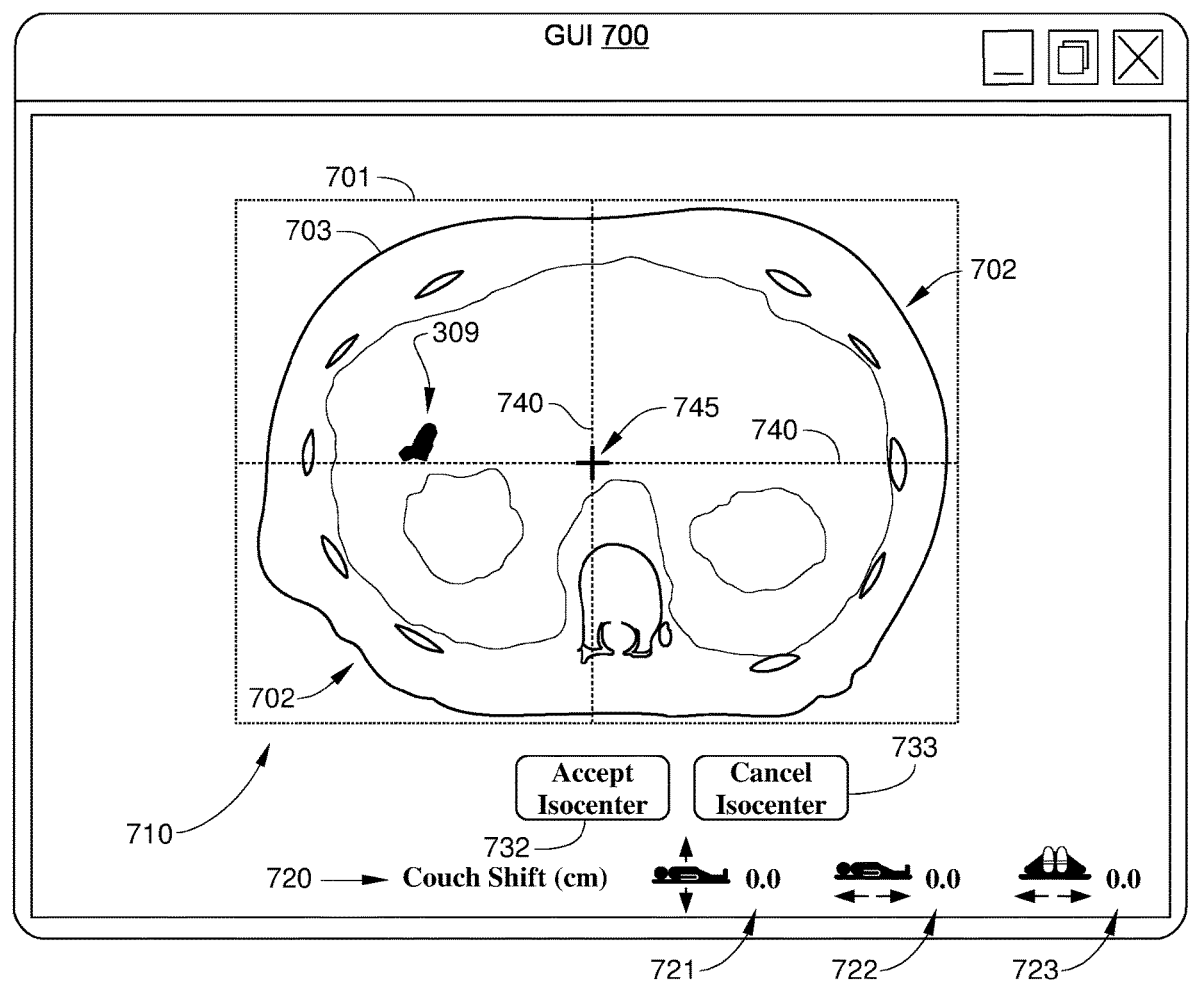
FIGS. 7A, 7B, and 7C schematically illustrate a graphical user interface displayed by a remote display screen of a radiation therapy system at certain steps of the method of FIG. 6.
Figure 7B:
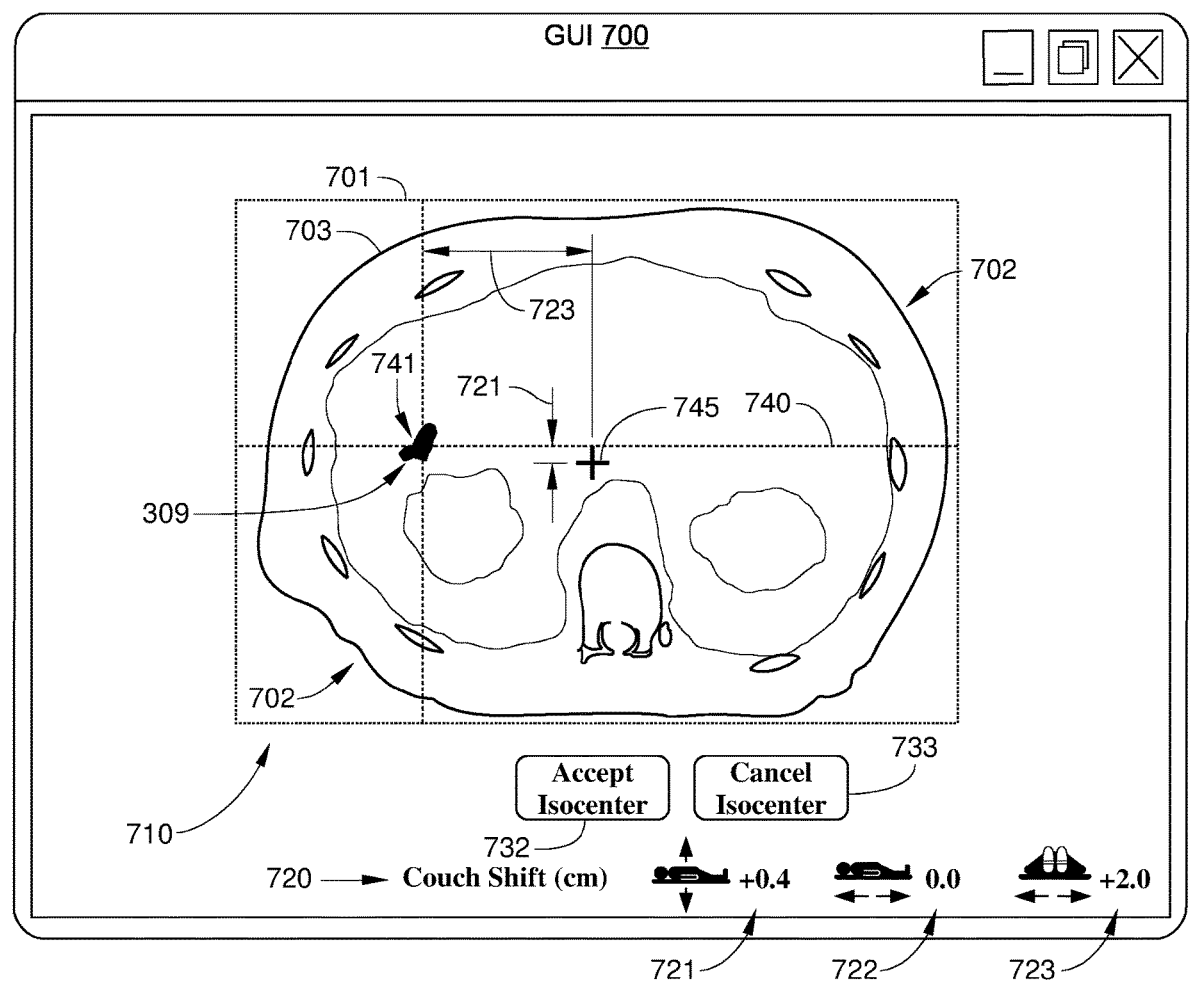
Figure 7C:
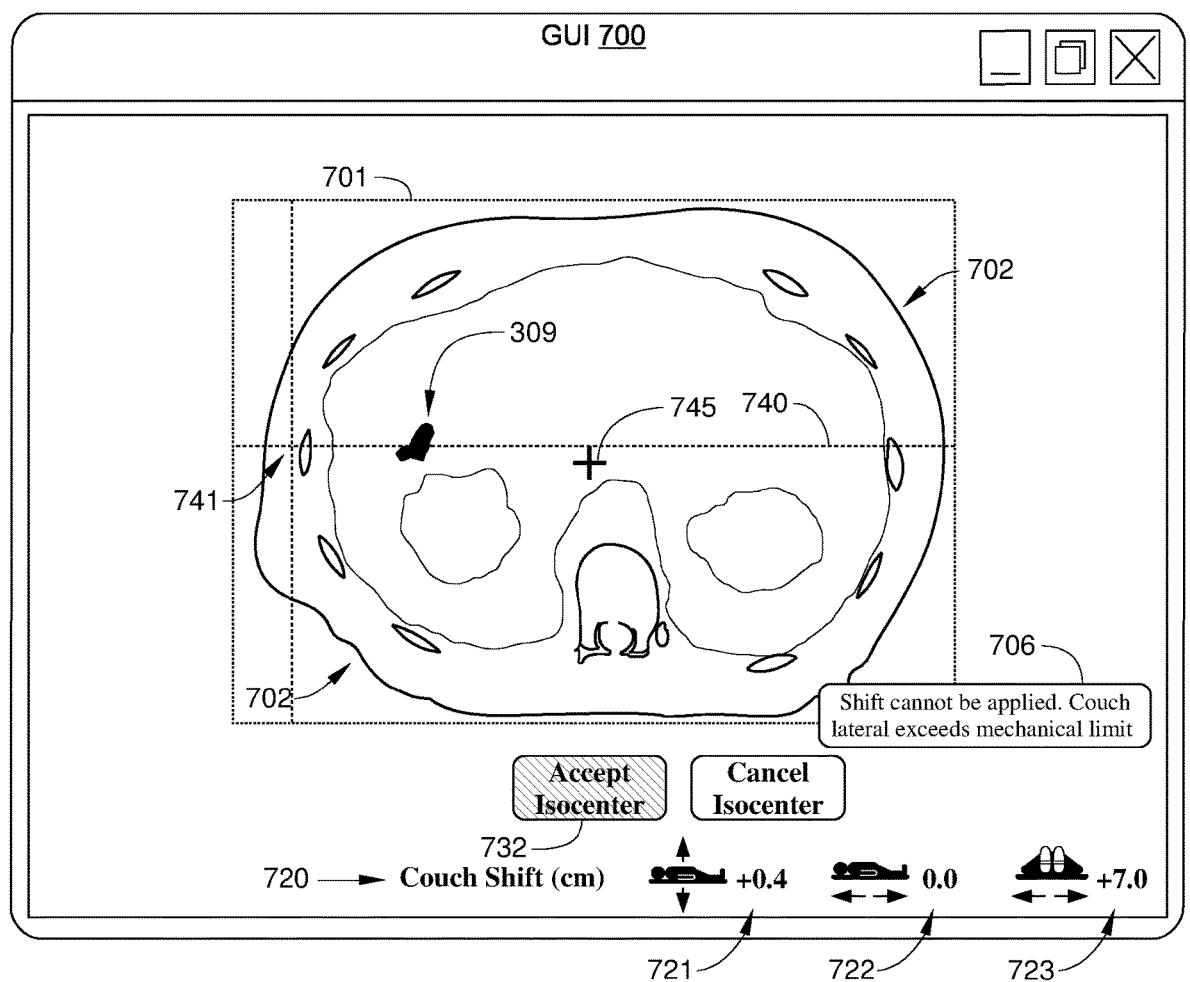
Figure 8A:
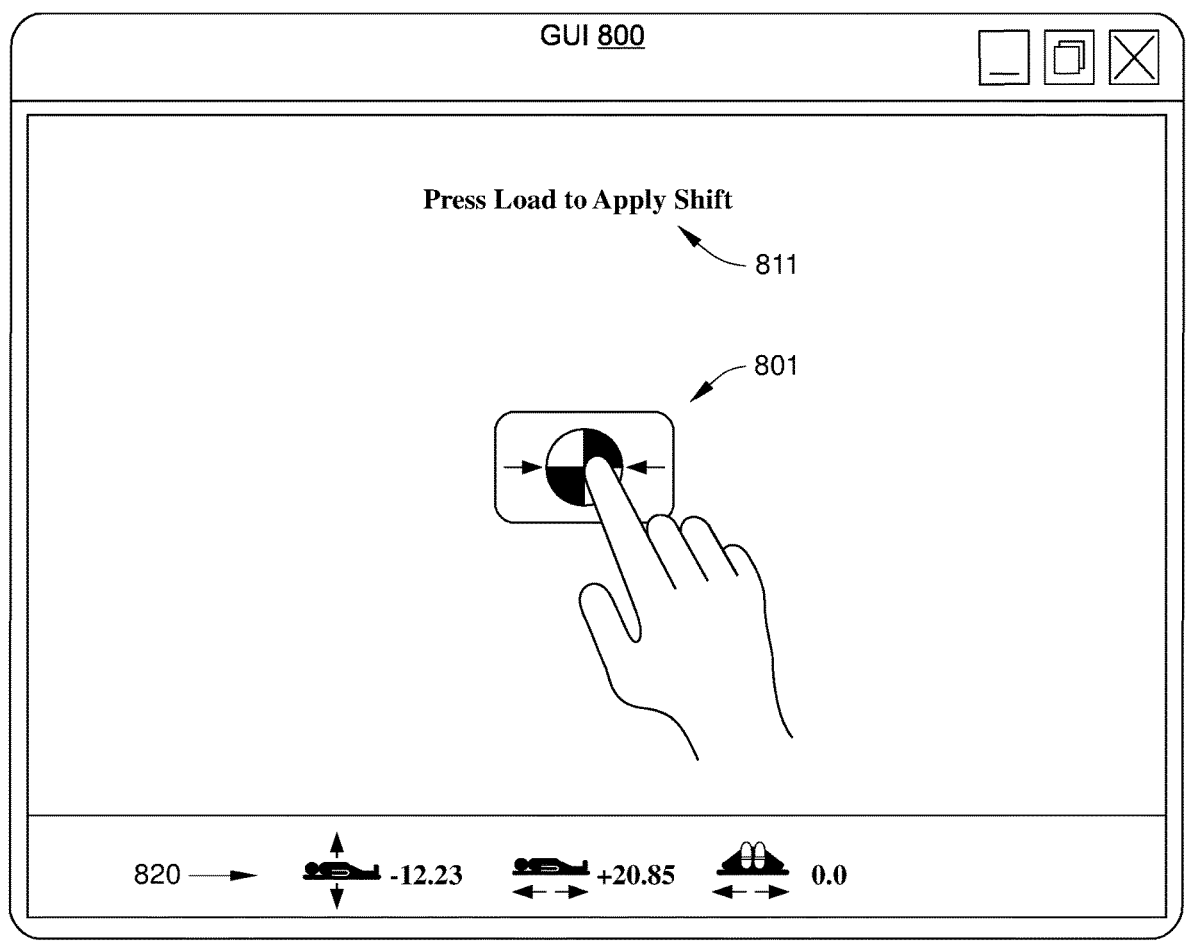
FIGS. 8A, 8B, and 8C schematically illustrate a graphical user interface displayed by a treatment room display screen of a radiation therapy system at certain steps of the method of FIG. 6, according to various embodiments.
Figure 8B:
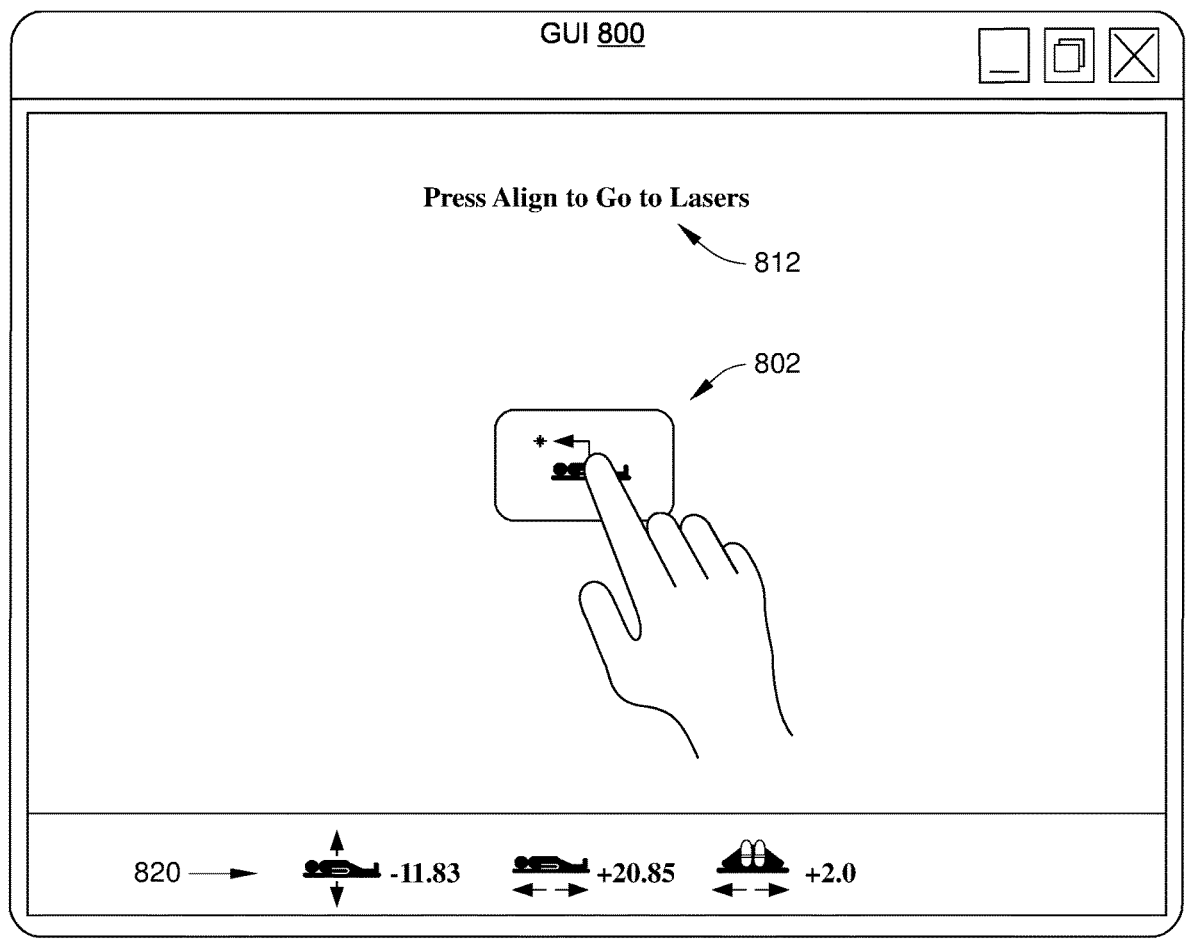
Figure 8C:
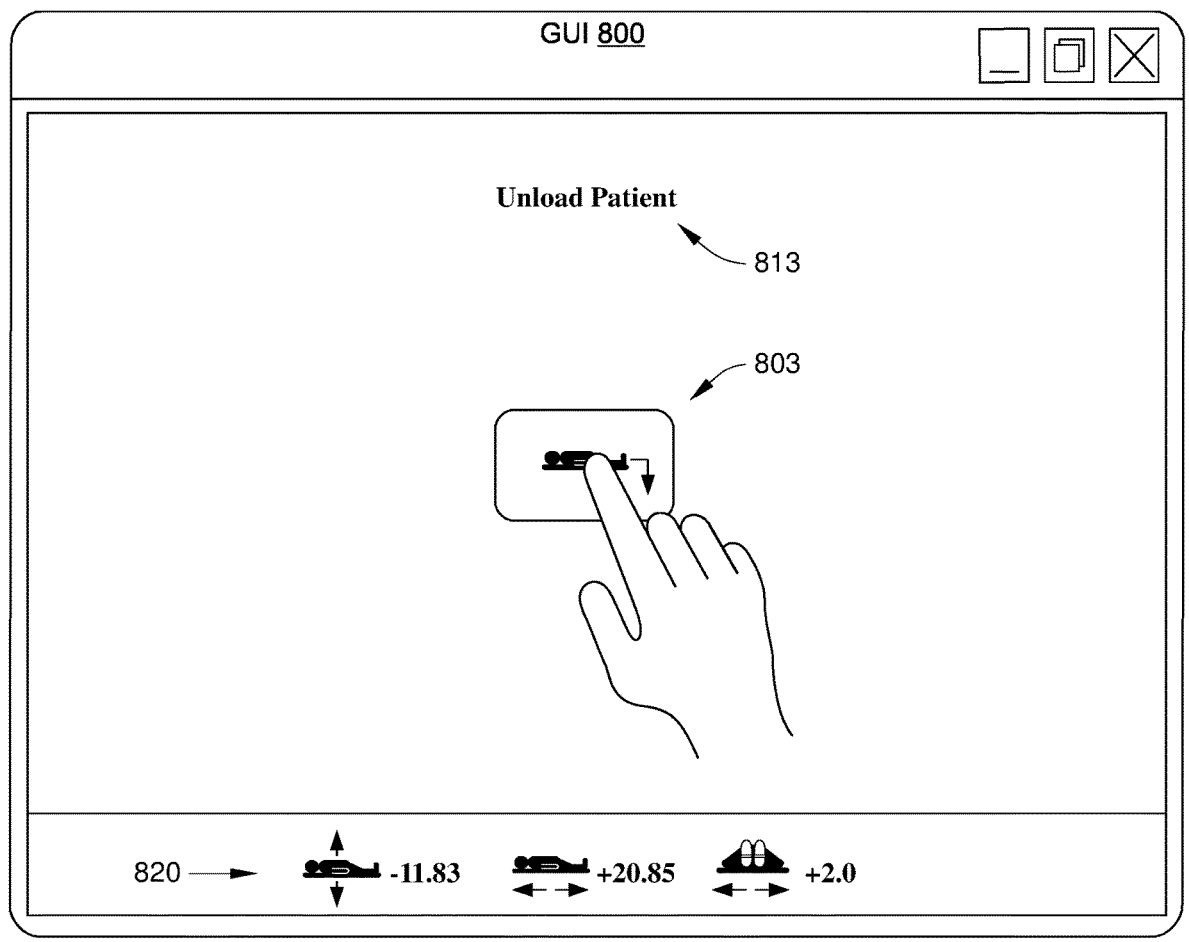

FIG. 6 sets forth a flowchart of a method 600, according to one or more embodiments. Method 600 may include one or more operations, functions, or actions as illustrated by one or more of blocks 601-650. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although method 600 is described in conjunction with RT system 110 and FIGS. 1, 2, 3, 4, and 5, persons skilled in the art will understand that any suitably configured radiation therapy system is within the scope of the present embodiments. FIGS. 7A, 7B, and 7C schematically illustrate a graphical user interface (GUI) 700 of RT system 110 displayed by a remote display screen at certain steps of method 600, according to various embodiments. FIGS. 8A, 8B, and 8C schematically illustrate a GUI 800 of RT system 110 displayed by a treatment room display screen at certain steps of method 600, according to various embodiments.

In step 601, RT system 110 generates treatment planning images. For example, in some embodiments, RT system 110 acquires a set of 2D projection images via a CBCT process of an anatomical region of a patient that includes target volume 309. In such embodiments, the set of 2D projection images can be combined, via a reconstruction process, to generate a three-dimensional digital volumetric image, as described in step 602. Prior to acquisition of the treatment planning images, a patient is positioned at an initial position on couch 207. In some instances, one or more immobilization and/or beam modification devices are also positioned with the patient on couch 207 or otherwise installed on RT system 110.

In step 602, RT system 110 reconstructs a digital volume based on the 2D projection images or other treatment planning images generated in step 601. For example, in some embodiments, the reconstruction is performed by one or more computing devices associated with image acquisition and treatment control computer 206 and/or remote control console 210. In some embodiments, the reconstructed volume 3D is a volumetric data set of the anatomical region. In some embodiments, a Feldkamp, Davis and Kress (FDK) reconstruction algorithm is employed to generate an initial reconstructed volume 621, and in other embodiments, any other suitable reconstruction algorithm is employed.

In step 603, RT system 110 displays a digital volume 701 or a selected portion of digital volume 701 of a region 702 of patient anatomy at a remote display screen, as shown in FIG. 7A. For example, in some embodiments, the remote display screen is a display screen associated with remote control console 210. Region 702 can be any technically feasible portion of patient anatomy, including the head, chest, abdomen, and the like. In the embodiment illustrated in FIGS. 7A, 7B, and 7C, digital volume 701 includes target volume 309 and extends to an edge surface 703 of region 702. Alternatively or additionally, in some embodiments, digital volume 701 does not include all of edge surface 703, or does not include any portion of edge surface 703.

In some embodiments, the portion of digital volume 701 displayed in GUI 700 includes one or more of a sagittal slice, a transversal slice, and/or a coronal slice of digital volume 701. In such embodiments, a user can visually determine a location of target volume 309 in three dimensions. For ease of description, in the embodiment illustrated in FIG. 7A, a single view of digital volume 701 is displayed in GUI 700, such as a transversal slice 710.

In the embodiment illustrated in FIG. 7A, GUI 700 also displays one or more user interface elements that display information for a user and/or are configured to receive a user input. In the embodiment illustrated in FIGS. 7A, 7B, and 7C, user interface elements displayed by GUI 700 include couch shift values 720, an Accept Isocenter button 732, a Cancel Isocenter button 733, and a patient origin selection cursor 740, among others. The user interface elements displayed by GUI 700 may be modified by any technically feasible user input approach, including via mouse motion and/or mouse clicks, a user gesture on a touch-sensitive screen, a keyboard input, a voice input, and/or the like. In the embodiment illustrated in FIG. 7A, patient origin selection cursor 740 is positioned at an initial patient origin 745, which corresponds to an imaging isocenter of RT system 110. Thus, initial patient origin 745 is generally located at a center location in the field of view of transversal slice 710.

The couch shift values 720 indicate a couch shift required to position a location currently indicated by patient origin selection cursor 740 to be positioned at an isocenter of RT system 110 during treatment. Thus, couch shift values 720 indicate a couch shift that is performed after couch 207 is unloaded from an imaging position of RT system 110 to an initial (or marking) position of RT system 110 and before external patient markings are placed on the patient. As a result, at time of treatment, once the patient is appropriately positioned on couch 207 via the external patient markings and couch 207 is moved to the treatment position, the location indicated by patient origin selection cursor 740 is generally positioned at the isocenter of RT system 110. Couch shift values 720 include a vertical shift value 721, a longitudinal shift value 722, and a lateral shift value 723. In the embodiment illustrated in FIG. 7A, vertical shift value 721, sagittal shift value 722, and lateral shift value 723 each have a value of 0.0, because patient origin selection cursor 740 is positioned at initial patient origin 745.

Accept Isocenter button 732 enables a user to define and accept a specific location for a patient origin in one or more slices of digital volume 701. Thus, Accept Isocenter button 732 changes the patient origin from initial patient origin 745 to the current position of patient origin selection cursor 740 in transversal slice 710. Cancel Isocenter button 733 enables a user to cancel a currently selected patient origin. Patient origin selection cursor 740 enables a user to indicate a particular position in a slice of digital volume 701 for selection. In some embodiments, couch shift values 720 are updated in real-time as patient origin selection cursor 740 is moved within a particular slice of digital volume 701. In other embodiments, couch shift values 720 are updated in response to a particular location within a particular slice of digital volume 701 being selected by Accept Isocenter button 732.

In step 604, RT system 110 receives a user input indicating a potential location of a patient origin via GUI 700. For example, in an embodiment, a user positions patient origin selection cursor 740 over target volume 309, as show in FIG. 7B. In the embodiment, the potential location of a patient origin is indicated by a center point 741 of patient origin selection cursor 740.

In step 605, RT system 110 determines couch shift values 720. As shown in FIG. 7B, couch shift values 720 correspond to the differences in position between center point 741 and initial patient origin 745. Because patient origin selection cursor 740 is positioned over target volume 309, the current values of couch shift values 720 correspond to a shift of couch 207 prior to the external markings being applied to the patient. As a result, at time of treatment, when the patient is positioned based on the external markings, the patient origin and target volume 309 are positioned at isocenter 303 of RT system 110 when the patient is positioned at a treatment position. In some embodiments, the determined couch shift parameters are updated in real-time, as shown in FIG. 7B, and show the current shift needed to locate center point 741 of patient origin selection cursor 740 at isocenter 303. In some embodiments, couch shift values 720 are tracked in a coordinate system common with LINAC 304.

In step 610, RT system 110 determines whether the couch shift values 720 determined in step 605 can be implemented by RT system 110. For example, for one-sided treatments in which couch 207 is not centered, such as breast and lung treatments, longitudinal shift value 722 can exceed the remaining range of lateral motion of couch 207. When RT system 110 determines that couch shift values 720 can be implemented, method 600 proceeds to step 621. When RT system 110 determines that couch shift values 720 cannot be implemented, method 600 proceeds to step 611. It is noted that the coordinate system employed to determine couch shift values 720 is the same coordinate system employed to move couch 207 to a treatment position at time of treatment. Thus, no conversion of coordinate systems takes place in step 605, and no transfer of couch shift values 720 is performed from an imaging system to RT system 110 in order to determine whether the couch shift values 720 determined in step 605 can be implemented by RT system 110.

In step 611, RT system 110 disables acceptance of couch shift values 270 associated with current location of center point 741. For example, in an embodiment, Accept Isocenter button 732 is grayed-out or otherwise disabled as user interface elements of GUI 700. Thus, because the current value of, for example, sagittal shift value 722, exceeds the remaining range of lateral motion of couch 207, RT system 110 prevents a user from marking or accepting the current location of center point cursor 741 as a patient origin. As a result, a patient origin that couch 207 cannot move to isocenter 303 of RT system 110 cannot be defined by the user, and the patient origin is not moved from initial patient origin 745.

In step 612, RT system 110 generates an alert for a user indicating that the current location of center point 741 cannot be selected as a patient origin. In some embodiments, the alert is generated via GUI 700, as shown in FIG. 7C. In the embodiment illustrated in FIG. 7C, an alert message 706 is displayed when RT system 110 determines that the current location of center point 741 cannot be selected as a patient origin. Alternatively or additionally, in some embodiments, the alert can be generated via one or more of an icon and/or text in GUI 700, a visual indicator external to GUI 700 (e.g., a light or illuminated icon), and/or an audible indicator external to GUI 700. Method 600 then proceeds to step 650 and terminates.

Step 621 is performed in response to RT system 110 determining that couch shift values 720 can be implemented by couch 207 and, therefore, current location of center point cursor 741 can be selected as a new patient origin. In step 621, RT system 110 enables acceptance via GUI 700 of the current location of center point 741 as a patient origin. For example, in some embodiments, in step 621, Accept Isocenter button 732 is made visible, is not grayed out, and/or is otherwise activated in GUI 700.

In step 622, RT system 110 receives a user input indicating acceptance of the current location of center point 741 as a patient origin via GUI 700. For example, in an embodiment, a user selects Accept Isocenter button 732. In step 622, RT system 110 accepts couch shift values 720 associated with the current location of center point 741 as the couch shift values for positioning target volume 309 at isocenter 303 during treatment.

In step 623, RT system 110 prompts the user to move enter the treatment room and apply couch shift values 720 via GUI 700. For example, in some embodiments, GUI 700 displays one or more of a textual prompt, an icon, an audible alert, and/or another indicator at the remote display screen.

In step 624, RT system 110 prompts the user at a treatment room display to apply couch shift values 720. For example, in some embodiments, the treatment room display screen is a display screen associated with image acquisition and treatment control computer 206, and prompts the user via GUI 800. In such embodiments, GUI 800 displays an indicator that a particular couch motion control 202 should be depressed or otherwise actuated, as shown in FIG. 8A. For example, in one such embodiment, GUI 800 displays an image of a load button 801 being depressed, where load button 801 is a couch motion control 202 that is generally employed for initiating movement of couch 207 to a loaded position so that the new patient origin that has replaced initial patient origin 745 is located at the geometric isocenter of RT system 110 (e.g., isocenter 303). Additionally or alternatively, in some embodiments, GUI 800 displays text directions 811 to prompt a user to apply couch shift values 720 when in the treatment room. Additionally or alternatively, in some embodiments, RT system 110 prompts the user to apply couch shift values 720 by making a particular couch motion control 202 visually more prominent than other couch motion controls, for example via flashing and/or color change. In some embodiments, GUI 800 also displays couch position values 820 that indicate a current position of couch 207 in the coordinate system of RT system 110.

In step 625, RT system 110 receives a user input to apply couch shift values 720 and move couch 207 to the loaded position, so that the new patient origin that has replaced initial patient origin 745 is disposed at isocenter 303 of RT system 110. It is noted that the radiation therapy position for the patient is determined in treatment planning, and is distinct from the loaded position described above. However, because definition of the new patient origin is based on analysis of digital volume 701, the new patient origin can frequently coincide with or be disposed in close proximity to the treatment planning volume. Thus, the likelihood of couch shifts being implemented during treatment planning to better position the treatment planning volume at isocenter 303 is greatly reduced. In some embodiments, the user input is received via GUI 800. In some embodiments, the user input is received via the couch motion control 202 indicated in step 624, such as load button 801.

In step 626, RT system 110 attempts to move couch 207 to the treatment position for the patient. It is noted that the patient remains disposed on couch 207 throughout method 600. Thus, step 626 allows a physical confirmation that couch 207 and the patient can be moved to the treatment position defined by couch shift values 720 without any collisions or other clearance issues. For example, the potential for collisions with patient extremities and/or accessories can be checked in step 626 while the patient is already correctly positioned on couch 207.

In step 630, RT system 110 determines whether couch shift values 720 have been applied successfully. For example, in some embodiments, when a collision is detected by RT system 110 while moving couch 207 and the patient to the treatment position, couch shift values 720 are determined to not be applied successfully. Additionally or alternatively, in some embodiments, when a user manually stops motion of couch 207, couch shift values 720 are determined to not be applied successfully. When RT system 110 determines that couch shift values 720 are not applied successfully, method 600 proceeds to step 631; when RT system 110 determines that couch shift values 720 are applied successfully, method 600 proceeds to step 641.

In step 631, RT system 110 halts motion of couch 207.

In step 632, RT system 110 generates an alert notifying the user that couch shift values 720 are not successfully applied. For example, in some embodiments, the alert can be generated via one or more icons and/or text in GUI 800, a visual indicator external to GUI 800 (e.g., a light or illuminated icon), and/or an audible indicator external to GUI 800. Method 600 then terminates.

In step 641, RT system 110 prompts the user at a treatment room display to move the patient to a marking position. In such embodiments, GUI 800 displays an indicator that a particular couch motion control 202 should be depressed or otherwise actuated, as shown in FIG. 8B. For example, in one such embodiment, GUI 800 displays an image of an alignment button 802 being depressed, where alignment button 802 is a couch motion control 202 that is generally employed for moving couch 207 and a patient to a marking position of RT system 110, sometimes referred to as a "virtual isocenter" of RT system 110. Additionally or alternatively, in some embodiments, RT system 110 prompts the user to move the patient to the marking position by making a particular couch motion control 202 visually more prominent than other couch motion controls, for example via flashing and/or color change. Additionally or alternatively, in some embodiments, GUI 800 displays a textual prompt 812 that prompts the user to move the patient to a marking position. In embodiments in which GUI 800 displays couch position values 820, couch position values 820 are updated to indicate that the current position of couch 207 in the coordinate system of RT system 110 has been modified by couch shift values 720.

In step 642, RT system 110 receives a user input from the treatment room to move couch 207 and the patient to the marking position. For example, in an embodiment, a user depresses or otherwise actuates alignment button 802. Additionally or alternatively, in some embodiments, the input is received at the treatment room display via GUI 800.

In step 643, RT system 110 moves couch 207 and patient to the marking position. A user in the treatment room can then apply external patient markings at locations indicated by setup lasers of RT system 110. After treatment planning is completed and the patient is repositioned on couch 207 for radiation treatment, alignment of the external patient markings applied in step 643 ensures that the patient origin selected in step 604 is located at isocenter 303 of RT system 110. It is noted that no translations or conversions of couch shift values 270 from one coordinate system to another is performed during or after method 600 to enable such an alignment process, since the coordinate system of the setup lasers of RT system 110 is shared with that of LINAC 304.

In step 644, RT system 110 prompts the user at the treatment room display to unload the patient. In such embodiments, GUI 800 displays an indicator that a particular couch motion control 202 should be depressed or otherwise actuated, as shown in FIG. 8C. For example, in one such embodiment, GUI 800 displays an image of an unload (or "home") button 803 being depressed, where unload button 803 is a couch motion control 202 that is generally employed to move couch 207 and a patient to an unload position of RT system 110, such as an initial position of couch 207. Additionally or alternatively, in some embodiments, RT system 110 prompts the user to unload the patient by making a particular couch motion control 202 visually more prominent than other couch motion controls, for example via flashing and/or color change. Additionally or alternatively, in some embodiments, GUI 800 displays a textual prompt 813 that prompts the user to unload the patient.

In step 645, RT system 110 transmits patient image information and couch coordinates to DICOM server 120. It is noted that couch coordinates transmitted to DICOM server 120 in step 645 are distinct from couch shift values 720 determined in step 605, but are based in part on couch shift values 720. In some embodiments, the patient image information includes digital volume 701 of region 702, the set of 2D projection images acquired in step 601, and/or patient origin information.

Step 650 is performed in response to RT system 110 determining that couch shift values 720 cannot be implemented by couch 207. In step 650, RT system 110 terminates method 600 and initiates repositioning and rescanning of the patient. For example, in some embodiments, RT system 110 also generates an alert or other notification regarding the issue that caused termination of method 600, such as shift values that cannot be implemented, a detected collision, and the like.

Application of Couch Shift Values

Figure 9:
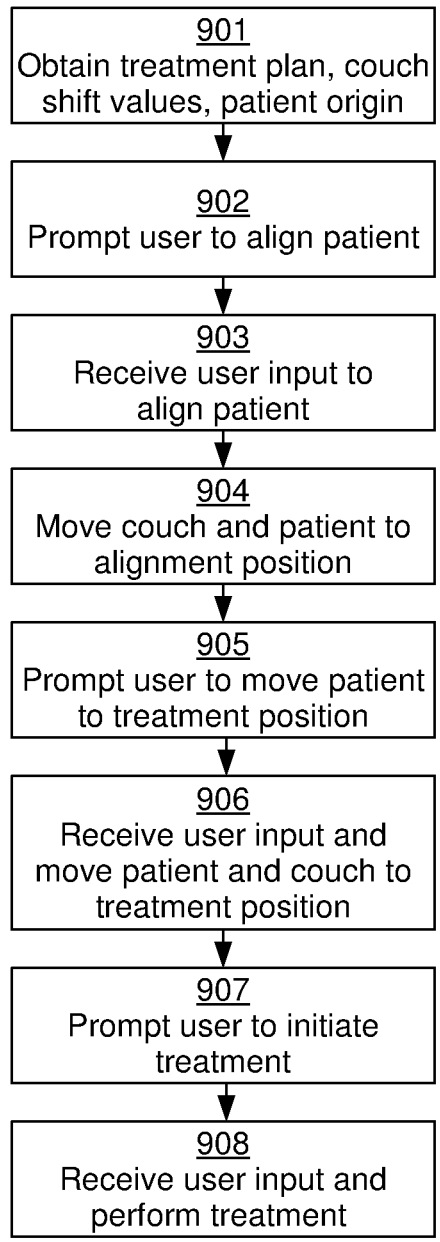
FIG. 9 sets forth a flowchart of a method for a radiation therapy system, according to one or more embodiments.

FIG. 9 sets forth a flowchart of a method 900 for a radiation therapy system, according to one or more embodiments. Method 900 may include one or more operations, functions, or actions as illustrated by one or more of blocks 901-908. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although method 900 is described in conjunction with RT system 110 and FIGS. 1-8C, persons skilled in the art will understand that any suitably configured radiation therapy system is within the scope of the present embodiments.

In step 901, RT system 110 retrieves or receives treatment plan information for a particular patient from DICOM server 120, including patient origin information and couch coordinates for the particular patient. Thus, RT system 110 obtains a treatment plan, couch coordinates, and patient origin information associated with the target volume 309 of the particular patient. In some embodiments, the couch coordinates received in step 901 include or are based in part on couch shift information generated in treatment or dosimetry planning. However, because the new patient origin included in the patient origin information is defined via method 600, the likelihood of such couch shifts being implemented during treatment planning to better position the treatment planning volume at isocenter 303 is greatly reduced.

In step 902, RT system 110 prompts the user to align the patient, for example via GUI 800.

In step 903, RT system 110 receives a user input to align the patient, for example, via GUI 800 and/or via one of couch motion controls 202, such as an alignment button.

In step 904, RT system 110 moves couch 207 and the patient to the alignment position, which is also referred to as the "virtual isocenter" of RT system 110. In some embodiments, once the patient and couch 207 are located at the alignment position, the patient position can be fine-tuned based on the setup lasers of RT system 110. Specifically, once the patient and couch 207 are located at the alignment position, the setup lasers of RT system 110 indicate the exact patient position required for the patient origin to be located at isocenter 303 during treatment.

In step 905, RT system 110 prompts the user to move the patient and couch 207 to the treatment position. In some embodiments, RT system 110 prompts the user to move the patient to the treatment position by making a particular couch motion control 202 visually more prominent than other couch motion controls, for example via flashing and/or color change.

In step 906, RT system 110 receives the user input to load the patient and loads the patient and couch 207. Specifically, RT system 110 moves couch 207 and the patient to the treatment position based on the couch coordinates included in or associated with the treatment plan received in step 901. Because the patient and couch 207 have been previously moved to the treatment position on RT system 110 prior to treatment planning, there is very little risk of collisions in step 906.

In step 907, RT system 110 prompts the user at the remote display screen to initiate treatment.

In step 908, RT system 110 receives the user input to initiate treatment and performs treatment while the patient is disposed at the treatment position. For example, in some embodiments, RT system 110 directs a treatment beam to isocenter 303 (and the patient origin included in the treatment plan) in accordance with the treatment plan received in step 901. As noted previously, the treatment plan received in step 901 is based in part on the patient origin information and couch shift values 270 determined via method 600 of FIG. 6.

Exemplary Computing Device

Figure 10:
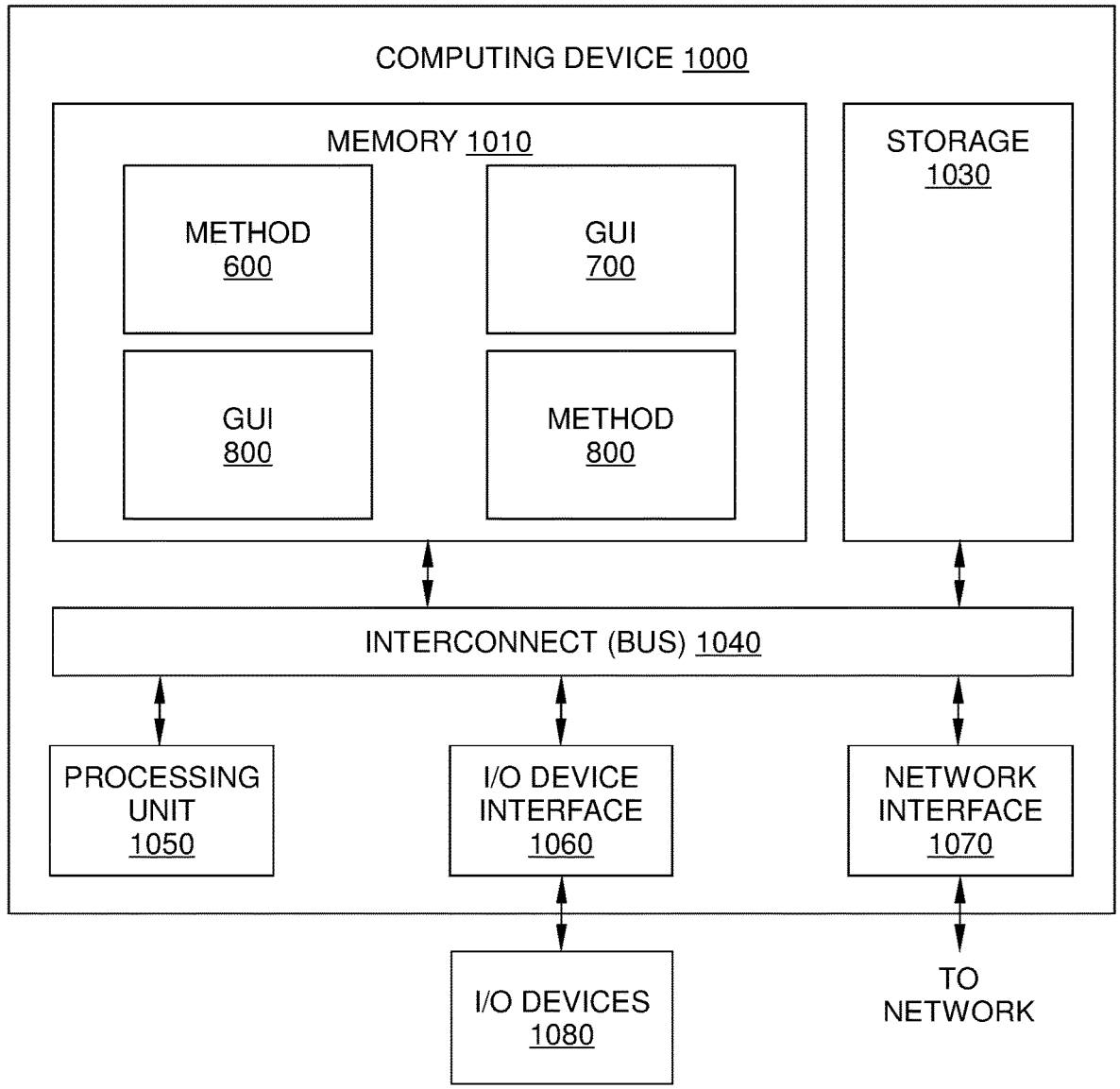
FIG. 10 is an illustration of a computing device configured to perform various embodiments of the present disclosure.

FIG. 10 is an illustration of computing device 1000 configured to perform various embodiments of the present disclosure. Thus, in some embodiments, computing device 1000 is implemented as or associated with image acquisition and treatment control computer 206 and/or remote control console 210. Additionally or alternatively, in some embodiments, computing device 1000 is implemented as or associated with DICOM server 120 and/or treatment planning system 130. Computing device 1000 may be a desktop computer, a laptop computer, a smart phone, or any other type of computing device suitable for practicing one or more embodiments of the present disclosure. In operation, computing device 1000 is configured to execute instructions associated with method 600, GUI 700, GUI 800, and/or method 900 as described herein. It is noted that the computing device described herein is illustrative and that any other technically feasible configurations fall within the scope of the present disclosure.

As shown, computing device 1000 includes, without limitation, an interconnect (bus) 1040 that connects a processing unit 1050, an input/output (I/O) device interface 1060 coupled to input/output (I/O) devices 1080, memory 1010, a storage 1030, and a network interface 1070. Processing unit 1050 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1050 may be any technically feasible hardware unit capable of processing data and/or executing software applications, including method 600, GUI 700, GUI 800, and/or method 900.

I/O devices 1080 may include devices capable of providing input, such as a keyboard, a mouse, a touch-sensitive screen, and so forth, as well as devices capable of providing output, such as a display device and the like. Additionally, I/O devices 1080 may include devices capable of both receiving input and providing output, such as a touchscreen, a universal serial bus (USB) port, and so forth. I/O devices 1080 may be configured to receive various types of input from an end-user of computing device 1000, and to also provide various types of output to the end-user of computing device 1000, such as displayed digital images or digital videos. In some embodiments, one or more of I/O devices 1080 are configured to couple computing device 1000 to a network.

Memory 1010 may include a random access memory (RAM) module, a flash memory unit, or any other type of memory unit or combination thereof. Processing unit 1050, I/O device interface 1060, and network interface 1070 are configured to read data from and write data to memory 1010. Memory 1010 includes various software programs that can be executed by processor 1050 and application data associated with said software programs, including method 600, GUI 700, GUI 800, and/or method 900.

Figure 11:
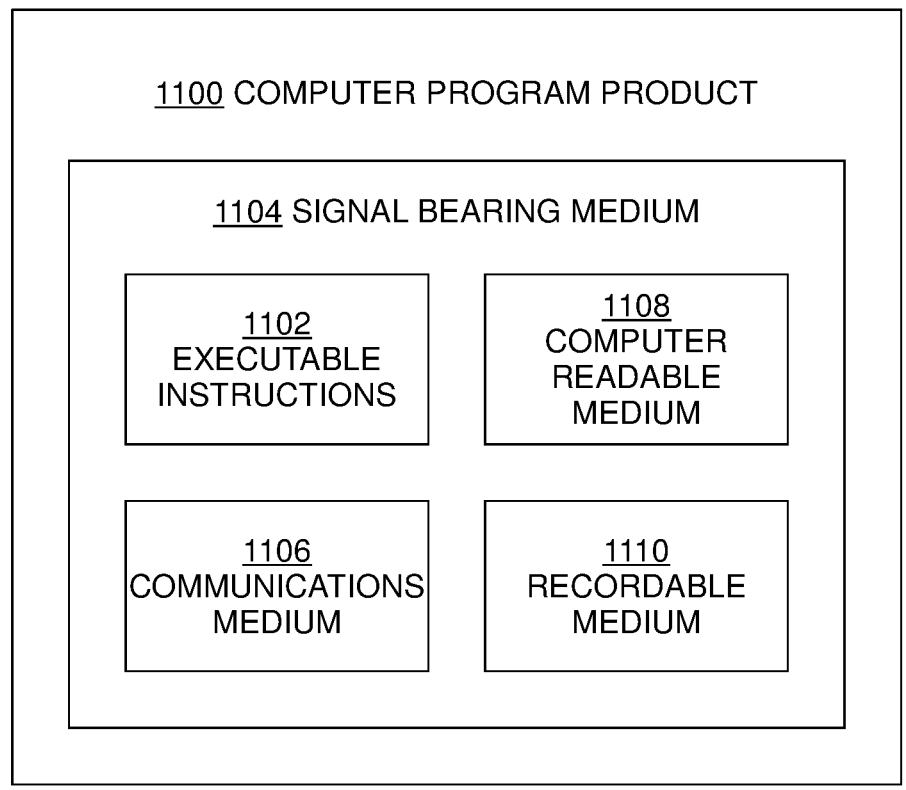
FIG. 11 is a block diagram of an illustrative embodiment of a computer program product for implementing one or more embodiments of the present disclosure.

FIG. 11 is a block diagram of an illustrative embodiment of a computer program product 1100 for implementing a method for segmenting an image, according to one or more embodiments of the present disclosure. Computer program product 1100 may include a signal bearing medium 1104. Signal bearing medium 1104 may include one or more sets of executable instructions 1102 that, when executed by, for example, a processor of a computing device, may provide at least the functionality described above with respect to FIGS. 1-10.

In some implementations, signal bearing medium 1104 may encompass a non-transitory computer readable medium 1108, such as, but not limited to, a hard disk drive, a Compact Disc (CD), a Digital Video Disk (DVD), a digital tape, memory, etc. In some implementations, signal bearing medium 1104 may encompass a recordable medium 1110, such as, but not limited to, memory, read/write (R/W) CDs, R/W DVDs, etc. In some implementations, signal bearing medium 1104 may encompass a communications medium 1106, such as, but not limited to, a digital and/or an analog communication medium (e.g., a fiber optic cable, a waveguide, a wired communications link, a wireless communication link, etc.). Computer program product 1100 may be recorded on non-transitory computer readable medium 1108 or another similar recordable medium 1110.

In sum, embodiments described herein reduce and/or eliminate motion artifacts that occur around moving high-contrast portions of patient anatomy. Further, in some instances, the embodiments reveal structures previously covered by such motion artifacts. Thus, the embodiments improve the perceived image quality of CBCT-based reconstructions and, in some instances improve accuracy in differentiating tissue types in a reconstructed CBCT image. Such improvements over prior art techniques may be employed in adaptive planning and/or during radiation therapy.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A method for a radiation therapy system that includes a movable couch to perform radiation therapy in a coordinate system, the method comprising:
based on X-ray images of an anatomical region of the patient that includes a target volume, reconstructing a digital volume of the anatomical region;
based on a user input indicating a location of a patient origin in the digital volume, determining one or more shift values for repositioning the patient origin at an isocenter of the radiation therapy system with respect to the coordinate system;
prior to transmitting the location of the patient origin in the digital volume to a treatment planning system, determining whether the movable couch can reposition the patient origin at the isocenter;
transmitting the location of the patient origin in the digital volume to the treatment planning system for generation of a treatment plan;
obtaining the treatment plan that is based on the location of the patient origin and is associated with the target volume;
based on the treatment plan, repositioning the movable couch so that the patient origin is disposed at the isocenter; and
while the patient origin is disposed at the isocenter, directing a treatment beam to the patient origin in accordance with the treatment plan associated with the target volume.

2. The method of claim 1, wherein transmitting the location of the patient origin in the digital volume to the treatment planning system external to the radiation therapy system occurs prior to obtaining the treatment plan.

3. The method of claim 1, further comprising, in response to determining that the movable couch cannot reposition the patient origin at the isocenter, generating an alert via a user interface of the radiation therapy system.

4. The method of claim 1, further comprising, while the patient is disposed on the movable couch, generating the X-ray images of the anatomical region.

5. The method of claim 1, wherein the patient origin is disposed within the target volume.

6. The method of claim 1, further comprising, prior to determining the one or more shift values for repositioning the patient origin, displaying a portion of the digital volume that includes the target volume.

7. The method of claim 6, wherein the portion of the digital volume comprises at least one of a sagittal slice of the digital volume, a transversal slice of the digital volume, and a coronal slice of the digital volume.

8. The method of claim 1, wherein the user input indicates the location of the patient origin within the digital volume with respect to the coordinate system.

9. A method for a radiation therapy system that includes a movable couch to perform radiation therapy, the method comprising:
based on X-ray images of an anatomical region of a patient disposed on the movable couch, wherein the anatomical region includes a target volume, reconstructing a digital volume of the anatomical region;
based on a user input indicating a location of a patient origin in the digital volume, determining one or more shift values for repositioning the patient origin at an isocenter of the radiation therapy system;
prior to transmitting the location of the patient origin in the digital volume to a treatment planning system, determining whether the movable couch can reposition the patient origin to the isocenter based on the one or more shift values;
transmitting the location of the patient origin in the digital volume to the treatment planning system for generation of a treatment plan; and
in response to determining that the movable couch cannot reposition the patient origin at the isocenter, generating an alert.

10. The method of claim 9, further comprising, in response to determining that the movable couch cannot reposition the patient origin at the isocenter, disabling a function associated with selecting the shift values.

11. The method of claim 10, wherein disabling the function associated with selecting the shift values includes disabling one or more user interface elements of a user interface of the radiation therapy system that are being displayed.

12. The method of claim 9, wherein generating the alert includes at least one of modifying a user interface element of a user interface of the radiation therapy system, adding a user interface element of the user interface, causing a visual indicator of the radiation therapy system to be activated, and causing an audible indicator of the radiation therapy system to be activated.

13. The method of claim 9, wherein each of the one or more shift values for repositioning the patient origin at the isocenter references a location in a coordinate system associated with the movable couch.

14. The method of claim 9, further comprising, while the patient is disposed on the movable couch, generating the X-ray images of the anatomical region.

15. The method of claim 9, further comprising, prior to receiving the user input, displaying a portion of the target volume within the digital volume.

16. The method of claim 15, wherein displaying the portion of the target volume within the digital volume comprises displaying the portion of the target volume with a display device associated with the radiation therapy system.

17. The method of claim 9, wherein the patient origin is disposed within the target volume.

18. A radiation therapy system, comprising:
a movable couch; and
a processor configured to:
based on X-ray images of an anatomical region of a patient disposed on the movable couch, wherein the anatomical region includes a target volume, reconstruct a digital volume of the anatomical region;
based on a user input indicating a location of a patient origin in the digital volume, determine one or more shift values for repositioning the patient origin at an isocenter of the radiation therapy system;
prior to transmitting the location of the patient origin in the digital volume to a treatment planning system, determine whether the movable couch can reposition the patient origin to the isocenter based on the one or more shift values;
transmit the location of the patient origin in the digital volume to the treatment planning system for generation of a treatment plan; and
in response to a determination that the movable couch is unable to reposition the patient origin at the isocenter, generate an alert.

19. The radiation therapy system of claim 18, wherein the process is further configured to, in response to the determination that the movable couch is unable reposition the patient origin at the isocenter, disable a function associated with selecting the shift values.

* * * * *